United States Patent [19]

Huber et al.

[11] Patent Number: 5,171,679
[45] Date of Patent: Dec. 15, 1992

[54] CYANOCOBALAMIN ACID HYDRAZIDES AND THEIR CONJUGATES

[75] Inventors: Erasmus Huber, Garching; Josef Dieckhoff, Feldafing; Christian Klein, Weilham; Konrad Kürzinger, Tutzing, all of Fed. Rep. of Germany

[73] Assignee: Boehringer Mannheim GmbH, Mannheim-Waldhof, Fed. Rep. of Germany

[21] Appl. No.: 461,215

[22] Filed: Jan. 5, 1990

[30] Foreign Application Priority Data

Jan. 11, 1989 [DE] Fed. Rep. of Germany ....... 3900648

[51] Int. Cl.$^5$ .................... C07K 17/06; C12N 9/02; C12N 9/16; C07H 23/00
[52] U.S. Cl. ...................................... 435/188; 536/25; 435/192; 435/196
[58] Field of Search ................. 536/25; 435/188, 192, 435/199; 530/395, 409

[56] References Cited

U.S. PATENT DOCUMENTS

| | | | |
|---|---|---|---|
| 3,920,631 | 11/1975 | Molteni et al. | 536/25 |
| 3,981,863 | 9/1976 | Niswender et al. | |
| 4,334,069 | 6/1982 | Buckler et al. | 544/237 |
| 4,550,163 | 10/1985 | Voss et al. | 544/244 |
| 4,925,931 | 5/1990 | McCully | 536/25 |

FOREIGN PATENT DOCUMENTS 0069450 1/1983 European Pat. Off.
2019176 11/1971 Fed. Rep. of Germany.

Primary Examiner—Johnnie R. Brown
Assistant Examiner—L. Eric Crane
Attorney, Agent, or Firm—Felfe & Lynch

[57] ABSTRACT

The present invention provides cobalamin acid hydrazides of the general formula:

$$B-CO-NH-NH(-R-CO-NH-NH)_xH \quad (I)$$

wherein B is a residue formed from a cobalamin by the splitting off of a $-CONH_2$ group, R is a spacer and x is 0 or 1, as well as a process for the preparation thereof.

The present invention also provides cobalamin conjugates of the general formula:

$$B-d-CO-NH-NH(-R-CO-NH)_xN=GP \quad (II)$$

in which B, R and x have the above-given meanings and d signifies the position of $-CO-NH-$, as well as a process for the preparation thereof. These cobalamin conjugates are very suitable for use in immunoassays, especially for the determination of cyanocobalamin.

12 Claims, 1 Drawing Sheet

FIGURE I

CYANOCOBALAMIN ACID HYDRAZIDES AND THEIR CONJUGATES

The present invention is concerned with new cobalamin acid hydrazides, especially cyanocobalamin acid hydrazides, and cobalamin conjugates derived therefrom.

The immunological determination of cobalamins (vitamin $B_{12}$) usually takes place in a competitive test in which the cobalamin of the sample and radioactively labelled cobalamin compete for a solid phasebound binding protein for cobalamin (intrinsic factor) (RIA test). After separation of the solid phase from the liquid phase, from the amount of radio-active labelling contained in one of the two phases can be determined the amount of cobalamin contained in the sample.

Because of the known disadvantages of RIA tests, for example radio-active exposure and disposal, it is desirable to replace the radio-active labelling by an enzymatic labelling.

Known coupling techniques such as have been described, for example, for the preparation of protein-vitamin $B_{12}$ conjugates as immunogens (cf. H. Gershman et al., Archives of Biochemistry and Biophysics, 153, 407/1972; D.F.M. v.d. Wiel et al., Clin Chim. Acta, 56, 143/1974; D.B. Endres et al., Clin Chem., 24/3, 460/1978; U.S. Pat. specification No. 3,981,863), do not result in stable $B_{12}$ derivatives. Corresponding processes have also been described for the preparation of $B_{12}$-enzyme conjugates.

Such prepared $B_{12}$ derivatives are sensitive to hydrolysis and can only be formulated as unstable intermediate stages. Therefore, the coupling yield is relatively low and, if at all, can only be reproduced with difficulty. In addition, a considerable polymerization of the enzyme takes place as a side reaction.

Therefore, it is an object of the present invention to provide cobalamine acid derivatives which can be isolated and are stable, which do not possess the above-mentioned disadvantages and can be obtained in a reproducible manner. This object is achieved by the new cobalamin acid hydrazides provided by the present invention.

Thus, according to the present invention, there are provided cobalamin acid hydrazides of the general formula:

$$B-CO-NH-NH \{R-CO-NH-NH\}_x H \qquad (I)$$

wherein B is a residue formed from cobalamin by splitting off a $-CONH_2$ group, R is a spacer and x is 0 or 1.

B is preferably the residue $B_{12}$ derived from cyanocobalamin and especially preferably these hydrazides have the general formula:

$$B-d-CO-NH-NH \{R-CO-NH-NH\}_x H \qquad (II)$$

wherein B, R and x have the above-given meanings and d is the position of $-CO-NH-NH-$.

In the case of these compounds, $-R-CO-$ signifies the radical $-CO-CH_2-O-CH_2-CH_2)_n O-CH_2-CO-$, in which n is 1, 2 or 3, and, in particular, they correspond to the general formula $B_{12}-d-CO-NH-NH_2$, in which $B_{12}$ and d have the above-given meanings, or to the general formula $B_{12}-d-CO-NH-NH-CO-CH_2-(O-CH_2-CH_2)_n O-CH_2-CO-NH-NH_2$, in which $B_{12}$ and d have the above-given meanings and n is 1, 2 or 3.

According to the present invention, the free carboxylic groups obtained from the acid amide groups $-CO-NH_2$ of cobalamines of the general formula (IIA):

wherein $R_1$ represents the various, different radicals of the individual cobalamins (in the case of cyanocobalamin, $R_1$ is CN; cf. for example, Römpps Chemio-Lexikon, Volume 2, 8th edition, pub. Franckh'sche Verlagshandlung, Stuttgart, page 784), are converted into the hydrazides of general formula (I).

The conversion of the acid amide group $-CO-NH_2$ into the free carboxyl group takes place in known manner by acidic saponification and isolation of the free carboxylic acids (cf. R. Yamada and H.P.C. Hogenkamp, J. Biol. Chem., 247, 6226–6270/1972; D. L. Anton et al., J.A.C.S., 102, 2215/1980). It is preferred to work in such a manner that an incomplete saponification of the acid amide groups present in the cobalamin molecule is achieved in order that only one or a few of the corresponding carboxyl groups are liberated. From the so obtained mixture can then be isolated in known manner the compound in which the free carboxyl group is present in a particular position. The compound with the free carboxyl group in the d-position (cf. the above-given formula for the cobalamins) is preferably isolated. These free carboxylic acids are then converted by further reaction into the corresponding hydrazide of general formula (I). It is also possible to start from a mixture of cobalamin carboxylic acids with the formation of a mixture of the corresponding hydrazides. For the preparation of a cobalamin conjugate for use in immunoassays, having regard to the sensitivity of the method of determination, it is advantageous and, therefore, in all cases preferable to start from a single purified carboxylic acid and to convert this into the corresponding pure and definite hydrazide.

The conversion of the free carboxylic acids into the corresponding hydrazides can take place with the use of known process steps. The cobalamin monocarboxylic acids are preferably converted into the carboxylic acid hydrazides of general formula (I) by reaction with a carbodiimide, for example N-ethyl-N'-(dimethylaminopropyl)-carbodiimide, and an appropriate hydrazine compound. The preparation of compounds of general formula (I), wherein x is 1, can take place by known process means also by a stepwise build-up of the grouping attached to B, for example with the reaction sequence B—COOH→B—CO—NH—NH—R—COOH→B—CO—NH—NH—R—CO—NH—NH$_2$, or, however, also by reaction with a compound of the general formula:

for example with triethylene glycol diacetic acid bishydrazide (TEDEH). The reaction conditions thereby correspond to those known and usual for such reactions.

Therefore, the present invention also provides a process for the preparation of the cobalamin acid hydrazides of general formula (I) according to the present invention, wherein, in a cobalamin carboxylic acid of the general formula B—COOH, the carboxyl group is converted in known manner, by reaction with a hydrazide, into a radical of the general formula:

whereby, when x is 1, the build up of this grouping can also take place stepwise. According to the process of the present invention, there are especially prepared the following especially preferred compounds of general formula (I) according to the present invention.

The carboxylic acid hydrazides of general formula (I) according to the present invention can be readily isolated and characterized. They are stable compounds which have a stable and, therefore, good storage stability.

Of the cobalamin hydrazides of general formula (I) according to the present invention, those are preferred in which the cobalamin residue B is the residue of methylcobalamin or especially of cyanocobalamin B$_{12}$. The acid hydrazide grouping —CO—NH—NH— is preferably present in the b-, e- and especially in the d-position (corresponds to the 3-, 13- and especially the 8-position of the —CH$_2$—CH$_2$—CO—NH$_2$— grouping in the corrin basic structure).

The spacer R can be, for example, an alkylene, aralkylene or arylene grouping which can also contain one or more heteroatoms. The grouping —R—CO— is preferably a diacyl residue derived from an alkylenedicarboxylic acid in which the alkylene moiety can be interrupted by one or more heteroatoms, especially —NH— or oxygen. In particular, the grouping —R—CO— can be a diacyl radical derived from a polyalkyleneglycol-, polyether, polyol- or polyester polyoldicarboxylic acid and, most preferably, a diacyl radical of the general formula:

wherein n is 3, derived from triethylene glycol diacetic acid (TEDE), but also a diacyl radical in which n is 1 or 2.

Of the compounds of general formula (I) according to the present invention, having regard to their use for the preparation of cobalamin-protein conjugates, there are, in the first place, to be mentioned B$_{12}$—d—CO—NH—NH$_2$ and B$_{12}$—d—CO—NH—NH—CO—CH$_2$—(O—CH$_2$—CH$_2$)$_n$O—CH$_2$—CO—NH—NH$_2$, wherein n is 1 or 2 and especially 3.

The cobalamin acid hydrazides of general formula (I) according to the present invention present a new form of activated cobalamins. Thus, the cobalamins of general formula (I) can, for example, be coupled directly and in high yields to oxidized glycosyl radicals of glycoproteins, for example peroxidase (POD). There are thereby obtained definite and readily characterizable conjugates which are stable to hydrolysis. At the same time, the immunological accessibility is thereby also high. This immunological accessibility can be increased in the cobalamin conjugates according to the present invention by elongating the hydrazo function with a spacer grouping R (cf. the following general formula (III), x=1). In this way, for example, the binding ability of the cobalamin hydrazides (hapten components) to an antibody can be further increased.

Therefore, the present invention also provides the cobalamin conjugates of the general formula:

(III)

wherein B, R and n have the above-given meanings and GP is the residue of a glycosyl group-containing protein which is bound via a glycosyl residue to the —NH—N= grouping.

B is preferably the residue B$_{12}$ derived from cyanocobalamin and especially preferably these hydrazides have the general formula:

(IV)

In the case of these compounds, —R—CO— especially signifies the radical —CO—CH$_2$—(O—CH$_2$—CH$_2$)$_n$O—CH$_2$—CO—, wherein n is 1, 2 or 3, and, in particular, they correspond to the formula B$_{12}$—d—CO—NH—N=GP or to the formula B$_{12}$—d—CO—NH—NH—CO—CH$_2$—(O—CH$_2$—CH$_2$)$_n$O—CH$_2$—CO—NH—N=GP, wherein n is 1, 2 or 3.

The glycoprotein residue GP can be derived from any appropriate glycoprotein or glycoproteid, for example from serum proteins, plasma proteins, glycoenzymes, antibodies, mucoproteids and the like. Preferred cobalamin conjugates according to the present invention are those which are derived from the abovementioned cobalamin acid hydrazides. As glycoprotein, there is preferably used a labelling enzyme, for example alkaline phosphatase (AP) and especially peroxidase (POD). Having regard to their suitability for use in immunoassays, there are especially to be mentioned B$_{12}$—d—CO—NH—N=GP and B$_{12}$—d—CO—NH—NH—CO—CH$_2$—(O—CH$_2$—CH$_2$)$_n$O—CH$_2$—CO—NH—N=GP, in which n is 1 or 2 and especially 3.

The preparation of the cobalamin conjugates of general formula (III) according to the present invention can take place by coupling (condensation) of the cobalamin acid hydrazides of general formula (I) with the hydroxyl groups of the glycosyl radicals of the glycoproteins after oxidation thereof, with the formation of the hydrazone grouping —NH—N=CH—glycoprotein. The reaction conditions thereby correspond to those which are usual for the preparation of hydrazones by condensation reactions.

Therefore, the present invention also provides a process for the preparation of cobalamin conjugates of the general formula (III), wherein a cobalamin acid hydrazide of general formula (I) according to the present invention is reacted in known manner with a glycoprotein in the oxidized form, with the formation of a hydrazone.

The cobalamin conjugates of general formula (III) according to the present invention are outstandingly suitable for use in the immunological determination of vitamin $B_{12}$. With the use of the cyanocobalamin conjugates according to the present invention and especially of $B_{12}$—d—CO—NH—NH—CO—CH$_2$—(O—CH$_2$—CH$_2$)$_3$O—CH$_2$—CO—NH—N=GP, there is possible, for example, a reproducible determination for vitamin $B_{12}$ (vitamin $B_{12}$ immunoassay) which is quick and easy to carry out with high sensitivity and exactitude.

Such a method of determination is the subject of Federal Republic of Germany Patent Application No. 3900650 entitled vitamin $B_{12}$ determination, the content of which is the subject of the present invention.

However, it is also possible to use the cobalamin conjugates according to the present invention in known processes for the determination of vitamin $B_{12}$ instead of radioactively-labelled vitamin $B_{12}$. Such suitable radioimmunoassays are described, for example, in Clinical Biochemistry, 18, 261-266/1985; U.S. Pat. specification No. 3,981,863; Clinica Chimica Acta, 56, 143-149/1974; Lit. Clin. Path. 20, 683-686/1967; and Brit. J. Haemat., 22, 21-31/1972.

Figure 1:
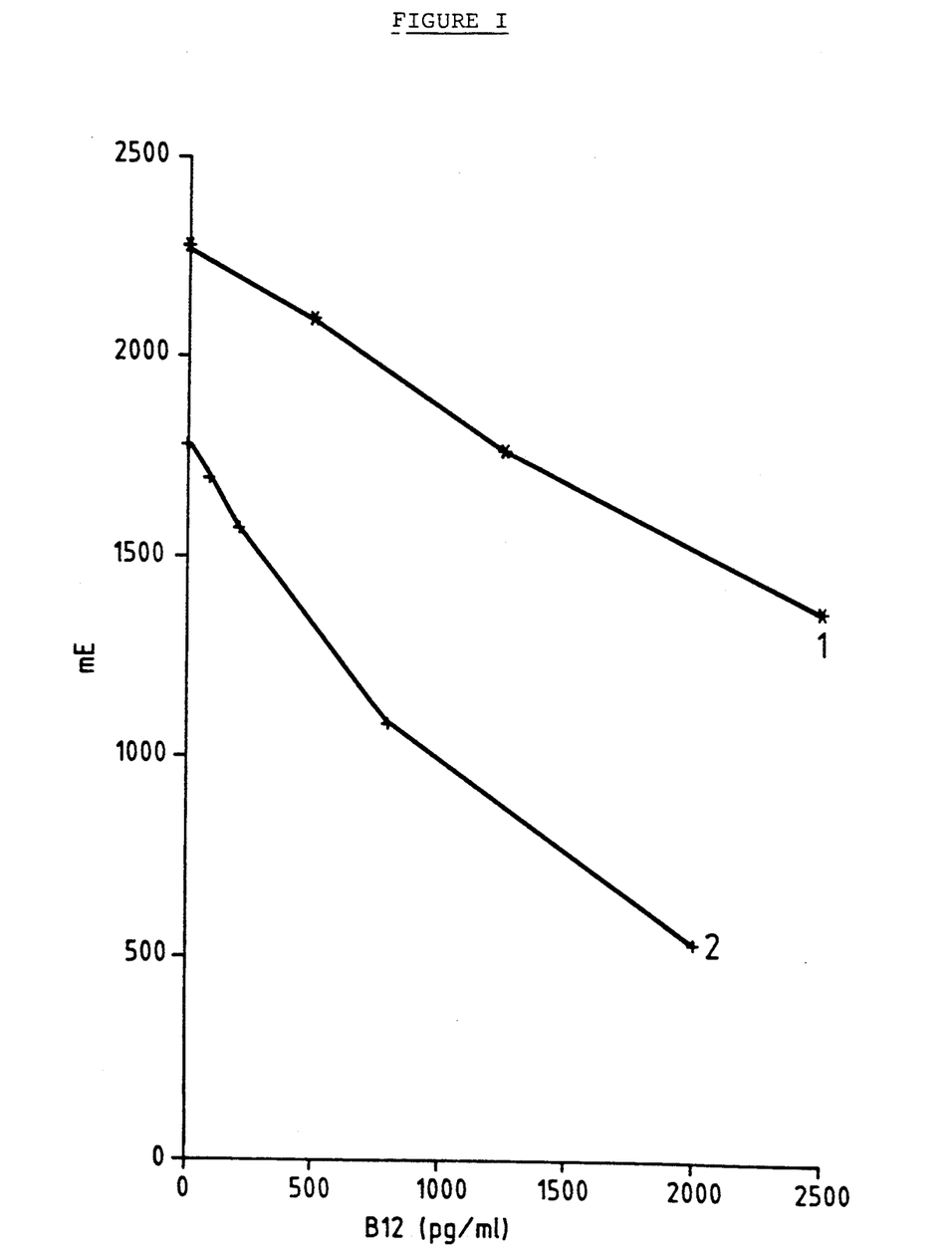

The following Examples are given for the purpose of illustrating the present invention, with reference to the accompanying drawing FIG. 1 which shows a comparison of the calibration curves for an enzyme immunoassay for vitamin $B_{12}$ with the use of a B12-enzyme conjugate of the present invention according to Example 5 (curve 2, activity 20 mU/ml.) and of a test using a conjugate according to Example 6 (curve 1, activity 90 mU/ml.); measurement wavelength 425 nm; E=extinction. It will be understood that the specification and examples are illustrative but not limitative of the present invention and that other embodiments within the spirit and scope of the invention will suggest themselves to those skilled in the art.

EXAMPLE 1

Preparation of triethyleneglycol diacetic acid bishydrazide (TEDEH)

TEDEH was prepared according to the following reaction scheme:

a) Bis-(tert.-butyl) triethylene glycol diacetate.(2)

33 g. (0.22 mole) Anhydrous triethylene glycol are dissolved in 300 ml. anhydrous dioxan and mixed portionwise, while stirring at ambient temperature, with 12 g. (0.4 mole) sodium hydride (20% in paraffin oil), a slight warming up to about 45° C. thereby taking place. The suspension is stirred for 3 hours at ambient temperature. Thereafter, while cooling with ice, 78 g. (0.4 mole) tert.-butyl bromoacetate are added dropwise thereto in the course of 1 hour. The suspension is further stirred for 16 hours at ambient temperature. Subsequently, the precipitated sodium bromide is separated off on a suction filter and the filtrate is evaporated under water pump vacuum. The oily residue is dissolved in 0.5 liters ethyl acetate, washed with 0.5 liters of water and the organic phase is dried with 30 g. anhydrous sodium sulphate. The solution is concentrated to a volume of about 100 ml. and applied to a column of silica gel (8.5×55 cm.). Elution is carried out with ethyl acetate and the individual fractions are examined by analytical thin layer chromatography (silica gel; elution agent: ethyl acetate). The polyethylene glycol derivative-containing fractions are made visible by spraying with Dragendorff reagent (see K. Thoma et al., Sci. Pharm., 32, 216/1964). The fractions containing the product (2) ($R_f$=0.60) are combined and evaporated under water pump vacuum. Yield: 19.2 g. of colourless oil; 23of theory.

b) Triethylene glycol-diacetic acid (3)

18.9 g. (50 mMole) of the ester (2) are dissolved at ambient temperature in 30 ml. trifluoroacetic acid and stirred for 2 hours. The solution is evaporated at 35° C. under water pump vacuum, the residue is digested three times with, in each case, 100 ml. diethyl ether and dried in a high vacuum at 45° C. The product (3) can be further used without further purification. Yield: 11.2 g. of colourless oil; 84% of theory.

TLC: silica gel; elution agent: ethyl acetate/methanol (4:1 v/v); $R_f$=0.08.

c) Triethylene glycol diacetic acid bis-(BOC-hydrazide) (4)

8.0 g. (30 mMole) of the dicarboxylic acid (3), together with 8.28 g. (72 mMole) N-hydroxysuccinimide, are dissolved in 200 ml. dry tetrahydrofuran and mixed with 14.8 g. (72 mMole) N,N'-dicyclohexylcarbodiimide in 50 ml. dry tetrahydrofuran at 20° C. with cooling in a waterbath. The solution is stirred for 20 hours at ambient temperature, the precipitated dicyclohexylurea is filtered off and the filtrate is evaporated in a vacuum. The viscous residue is dissolved in 100 ml. ethyl acetate, the solution is filtered and again evaporated. The last procedure is repeated twice and the residue is digested in 50 ml. isopropanol and dried in a high vacuum. The viscous oil obtained (about 9 g.) is dissolved in 60 ml. anhydrous chloroform and mixed, while stirring at ambient temperature, with 7.9 g. (60 mMole) tert.-butyl carbazate (BOC-hydrazine). The reaction mixture, which initially warms up slightly, is stirred for 20 hours at ambient temperature. Thereafter, it is washed twice with, in each case, 100 ml. of water, dried with 5 g. anhydrous sodium sulphate and the solution is evaporated under water pump vacuum. Yield: 9.2 g. of a viscous, slightly yellowish oil (60% of theory).

TLC: silica gel; elution agent: ethyl acetate/methanol (4:1 v/v); $R_f$=0.52.

d) Triethylene glycol diacetic acid bis-hydrazide hydrochloride (5)

5.1 g. (10 mMole) of compound (4) are dissolved in 20 ml. trifluoroacetic acid and stirred for 2 hours at ambient temperature. Thereafter, the solution is evaporated at 35° C. under water pump vacuum, the residue is dissolved in 80 ml. anhydrous ethyl acetate and gaseous hydrogen chloride passed through the solution for 10 minutes while cooling to 0° C. A precipitate of solid carboxylic acid hydrazide hydrochloride (5) is thereby formed. The suspension is left to stand for 2 hours at 0° C., subsequently filtered off with suction and the hygroscopic salt obtained is washed with 40 ml. anhydrous ethyl acetate. It is dried over anhydrous calcium chloride in a desiccator under high vacuum. Yield: 2.8 g. of a pale brown powder (75% of theory).

TLC: silica gel; elution agent: n-butanol/glacial acetic acid/water 50/15/25 v/v/v); $R_f$=0.45.

EXAMPLE 2

Cyanocobalamin-d-acid hydrazide ($B_{12}$-d-CO—NH—$NH_2$)

135 g. (0.1 mMole) cyanocobalamin-d-acid, together with 46 mg. (0.4 mMole) N-hydroxysuccinimide, are dissolved in 10 ml. of a mixture of dimethylformamide/water (1:1 v/v) and mixed with 98 mg. sodium cyanide. The solution is adjusted to pH 6 with 1 mole/liter sodium hydroxide solution. To the solution are added 77 mg. (0.4 mMole) N-ethyl-N'-dimethylaminopropylcarbodiimide hydrochloride (EDC) and 650 mg. (5 mMole) hydrazinium sulphate. The pH value is readjusted with a solution of sodium hydroxide, subsequently the reaction vessel is protected from light and the solution is stirred at ambient temperature. At intervals of 6 to 14 hours, there are added five times 46 mg. portions of N-hydroxysuccinimide and 77 mg. EDC to the reaction solution, the pH value thereby being readjusted each time to 6. After a total reaction period of 4 days, the reaction mixture is evaporated under a high vacuum, the residue is digested with 10 ml. tetrahydrofuran and filtered off over a suction filter. The solid residue is dissolved in 10 ml. of water and applied to a chromatography column (styrene-divinylbenzene copolymer; Amberlite ® XAD-2; volume 100 ml.). The salt impurities are washed from the column with 300 ml. of water and subsequently the crude product is eluted with 300 ml. methanol. The solution is evaporated under water pump vacuum, the residue is dissolved in 10 ml. of water and applied to a column of Dowex ® 1×2 (acidic ion exchanger, acetate form, 80 ml.). The end product is eluted with 250 ml. of water, unreacted acid thereby remaining behind in the column: it can subsequently be eluted with 0.04 mole/liter sodium acetate buffer (pH 4.7). The fractions containing the product are combined and lyophilized. Yield: 84 g. of cherry red powder; 60% of theory.

In the same way, starting from methyl-cobalamin-d-acid, there is obtained methyl-cobalamin-d-acid hydrazide.

EXAMPLE 3

Preparation of cyanocobalamin-d-acid hydrazide-POD-conjugate ($B_{12}$-d-CO—NH—N=POD).

30 mg. Horse radish peroxidase (POD; EC 1.11.1.7) are dissolved in 4.5 ml. of 0.03 mole/liter sodium acetate buffer (pH 5.5). 0.6 ml. of 0.2 mole/liter sodium periodate solution in 0.03 mole/liter sodium acetate buffer (pH 5.5) is added thereto, followed by stirring for 1 hour at ambient temperature. Thereafter, the solution is applied to a column of Sephadex-G-25 (moleculer sieve; volume 50 ml.) and eluted with 0.03 mole/liter sodium acetate buffer (pH 5.5) (detection at 403 nm). The protein-containing fractions are combined and mixed with 2.7 mg. $B_{12}$-d-CO—NH—$NH_2$ from Example 2. The reaction mixture is stirred for 16 hours at room temperature and the mixture then applied to a column of Ultragel-AcA-202 (molecular sieve; volume 80 ml.). Elution is carried out with 0.03 mole/liter sodium acetate buffer (pH 5.5) (detection=403 nm). The fractions containing the end product are combined, dialyzed for 6 hours against water and subsequently lyophilized. Yield: 26 mg.; 87% of theory.

EXAMPLE 4

Preparation of cyanocobalamin-d-acid-TEDEH
($B_{12}$-d-CO—NH—NH—CO—$CH_2$(O—$CH_2$—$CH_2$-$)_3$O—$CH_2$—CO—NH—$NH_2$)

135 mg. (0.1 mMole) Cyanocobalamin-d-acid, together with 46 mg. (0.4 mMole) N-hydroxysuccinimide, are dissolved in 10 ml. of a mixture of dimethylformamide­water (1:1 v/v) and mixed with 98 mg. sodium cyanide. The solution is adjusted to pH 5.5 with 1 mole/liter sodium hydroxide solution. To the solution are added 77 mg. (0.4 mMole) N-ethyl-N'-dimethylaminopropylcarbodiimide hydrochloride (EDC) and 1.84 g. (5 mMole) TEDEH hydrochloride. The pH value is readjusted with a solution of sodium hydroxide, subsequently the reaction vessel is protected from light and the solution is stirred at ambient temperature. At intervals of 6 to 14 hours, there are added five times 46 mg. amounts of N-hydroxysuccinimide and 77 mg. EDC to the reaction solution, the pH value being readjusted each time to a pH value of 5.5. After a total reaction time of 4 days, the reaction mixture is evaporated in a high vacuum, the residue is digested with 10 ml. acetone and the solvent then decanted off. The almost solid residue is dissolved in 10 ml. of water and applied to a column of Amberlite ®-XAD-2 (volume 100 ml.). The salt impurities are washed from the column with 300 ml. of water and subsequently the crude product is eluted with 300 ml. methanol. The solution is evaporated under water pump vacuum, the residue is dissolved in 10 ml. of water and applied to a column of Dowex ®-1×2 (acetate form; volume 80 ml.). The end product is eluted with 250 ml. of water, the unreacted acid thereby remaining behind on the column: it can subsequently be eluted with 0.04 mole/liter sodium acetate buffer (pH 4.7). The fractions containing the product are combined and lyophilized. Yield: 75 mg. of cherry red, readily hygroscopic powder; 46% of theory.

In the same way, starting from methyl-cobalamin-d-acid, there is obtained methylcobalamin-d-acid-TEDEH.

EXAMPLE 5

Preparation of cyanocobalamin-d-acid-TEDEH-POD conjugate
($B_{12}$-d-CO—NH—NH—CO—$CH_2$(O—$CH_2CH_2$-$)_3$—O—$CH_2$—CO—NH—N=POD)

30 mg. Horse radish peroxidase are dissolved in 4.5 ml. 0.03 mole/liter sodium acetate buffer (pH 5.5). 0.6 ml. of 0.2 mole/liter sodium periodate solution in 0.03 mole/liter sodium acetate buffer (pH 5.5) is added thereto and the reaction mixture is stirred for 1 hour at ambient temperature. Thereafter, the solution is applied to a column of Sephadex ®-G-25 (volume 50 ml.) and eluted with 0.03 mole/litre sodium acetate buffer (pH 5.5) (detection at $\nu$=403 nm). The protein-containing fractions are combined and mixed with 2.7 mg. of the hydrazide from Example 4. The reaction mixture is stirred for 16 hours at ambient temperature and then applied to a column of Ultragel ®-AcA-202 (volume 80 ml.). It is eluted with 0.03 mole/liter sodium acetate buffer (pH 5.5) (detection at $\nu$=403 nm). The fractions containing the end product are combined, dialyzed against water for 6 hours and subsequently lyophilized. Yield 27 mg. (90% of theory).

Analogously to the processes described in the preceding Examples 3 and 5 for the preparation of POD conjugates, with the use of other glycosylated labelling enzymes, for example alkaline phosphatase (AP), there can be prepared the corresponding conjugates.

EXAMPLE 6

Preparation of cyanocobalamin-d-monocarboxylic acid-POD conjugate (comparison compound)

The preparation is carried out in the manner described in Clin. Chim. Acta, 56, 143–149/1974.

For this purpose, $B_{12}$-monocarboxylic acid is prepared in the manner described in J.A.C.S., 102, 2215/1980.

100 mg. POD and 10 mg. vitamin $B_{12}$ are dissolved in 2.5 ml. phosphate buffer (0.07 mole/liter; pH 8.2) and 25 mg. carbodiimide added thereto. The solution is stirred for 72 hours at 4° C. and subsequently dialyzed against deionized water for 72 hours.

The purification of the conjugate takes place in the manner described in Example 5.

EXAMPLE 7

Determination of vitamin $B_{12}$ a) Sample preparation

250 $\mu$l. of human serum are mixed with 125 $\mu$l. dissolving reagent, consisting of 8 mg./ml. liponic acid and 1 mg./ml. potassium cyanide dissolved in 0.5 mole/liter sodium hydroxide solution, and incubated for 15 minutes at ambient temperature. Subsequently, 125 $\mu$l. of 200 mMol3/liter phosphate buffer (pH 4.1) are added thereto.

b) Reagents

Polystyrene test tubes coated with thermo-BSA streptavidin are prepared according to European Patent Specification No. 0,269,092.

Reagent 1

95 ng./ml. biotinylated monoclonal antibodies against vitamin $B_{12}$ (biotinylation according to J.A.C.S., 100, 3585-35900/1978).

Cell lines which produce suitable monoclonal antibodies have been deposited with the European Collection of Animal Cell Cultures (ECACC), Porton Down, Great Britain, under the numbers ECACC 88101301 and ECACC 88101302.

40 mMole/liter phosphate buffer (pH 7.2).

Reagent 2

$B_{12}$—d—CO—NH—NH—CO—$CH_2$(-O—$CH_2$—$CH_2$)$_3$O—$CH_2$—CO—NH—N=POD Activity about 20 mU/ml.). 40 mMole/liter phosphate buffer (pH 7.2).

Reagent 3

100 mMole/liter phosphate-citrate buffer (pH 4.4) 1.9 mMole/liter ABTS ® (2,2''-azino-di-(3-ethylbenzthiazoline-sulphonate) 3.2 mMole/liter sodium perborate c) Carrying out of the determination For carrying out the determination, 200 μl. of sample are introduced with 800 μl. Reagent 1 into a streptavidin tube and incubated for 60 minutes at ambient temperature. Subsequently, washing is carried out with a washing solution (250 mg./ml. sodium chloride and 1 mg./100 ml. copper sulphate), 1000 μl. of Reagent 2 solution are added thereto and incubation carried out for 30 minutes at ambient temperature. Washing is then carried out with a washing solution (250 mg./ml. sodium chloride and 1 mg./100 ml. copper sulphate) and 1000 μl. of Reagent 3 added thereto and incubation carried out for 30 minutes at ambient temperature and the colour formed measured as a measure for the vitamin $B_{12}$ content at 420 nm.

FIG. 1 of the accompanying drawing shows the calibration curve thereby obtained in comparison with a calibration curve for a test according to Example 6. For the production of the calibration curve, instead of the serum sample, there are used standards which consist of cyanocobalamin in 40 mMole/liter phosphate buffer (pH 7.2) with 0.9% sodium chloride, 0.9% crotein C and 0.1% potassium chloride.

EXAMPLE 8

Determination of vitamin $B_{12}$ (comparison example)

A vitamin $B_{12}$ determination is carried out in the manner described in Example 7, the there-mentioned standards thereby being used. Instead of the conjugate according to the present invention used in Reagent 2, there is used a POD conjugate according to Example 6 with an activity of about 90 mU/ml.

FIG. 1 shows a comparison of the calibration curves of a vitamin $B_{12}$ determination according to Example 7 and Example 8. This shows that with the conjugate according to Example 6, in spite of the higher activity, there is obtained a calibration curve which is flatter than that obtained with the conjugate according to the present invention.

We claim:

1. Cobalamin conjugates of the formula:

B—CO—NH(NH—R—CO—NH)$_x$N=GP  (III)

wherein B—CO— is a residue formed from a cobalamin of the formula (IIA)

by the hydrolysis of the —CONH$_2$ group (b), (d) or (e), $R^1$ is a cyano residue, R is a spacer, x is 0 or 1 and GP is the residue of a glycosyl group-containing protein which is bound via a glycosyl residue to the NH—N= grouping.

2. $B_{12}$—d—CO—NH—N=GP.

3. $B_{12}$—d—CO—NH—NH—CO—CH$_2$—(O—CH$_2$—CH$_2$)$_n$O—CH$_2$—CO—NH—N=GP in which n is 1, 2 or 3.

4. Cobalamine conjugates of the formula

B—CO—NH(NH—R—CO—NH)$_x$N=GP wherein GP is a peroxidase or an alkaline phosphatase bound via a glycosyl residue to the —N-H—N= group, B is $B_{12}$, R is a spacer and X is 0 or 1.

5. Cobalamin conjugates according to any one of claims 1, 2 or 3, wherein GP is the residue of a labelling enzyme.

6. Cobalamin conjugates according to claim 1 wherein —R—CO— is —CO—CH$_2$ (O—CH$_2$—CH$_2$)$_n$ O—CH$_2$—CO— in which n is 1, 2 or 3.

7. Cobalamin conjugates according to claim 1 of the general formula:

B—d—CO—NH—NH—R—CO—NH)$_x$N=GP  (IV)

wherein B, R and x have the same meanings as in claim 8 and d signifies the position of the B—d—CO—NH— as in the formula -continued wherein R¹ is a cyano residue.

8. The compound of claim 1 wherein R is
—CO—CH₂—O—(CH₂—CH₂—O)₃—CH₂.

9. Cobalamin conjugates according to claim 7 wherein —R—CO— is —CO—CH₂(OCH₂CH₂-)ₙOCH₂—CO— in which n is 1, 2 or 3.

10. Cobalamin conjugates according to claim 7 wherein GP is the residue of a labelling enzyme.

11. Process for the preparation of a cobalamin conjugate of formula III wherein B—CO— is a residue formed from a cobalamin of the formula by the hydrolysis of the CONH₂ group (b), (d) or (e), R¹ is a cyano residue, R is a spacer, x is 0 or 1 and GP is the residue of a glycosyl group-containing protein selected from the group consisting of a peroxidase or an alkaline phosphatase which is bound via a glycosyl residue to the NH—N= grouping comprising reacting a cobalamin acid hydrazide of the formula B—CO—NH—NH (R—CO—NH—NH)ₓH (I) with an oxidized glycosyl radical of a glycoprotein to form a hydrazone.

12. Process for the introduction of a spacer grouping into cobalamin conjugates according to claim 11 comprising introducing triethylene glycol diacetic acid bishydrazide as a spacer group.

* * * * *

UNITED STATES PATENT AND TRADEMARK OFFICE
CERTIFICATE OF CORRECTION

PATENT NO. : 5,171,679

DATED : December 15, 1992

INVENTOR(S) : Erasmus Huber, et al.

It is certified that error appears in the above-identified patent and that said Letters Patent is hereby corrected as shown below:

Col. 1, line 63:     after "CO-CH$_2$-" insert -- ƒ --.

Col. 2, formula (11A) (line 24):     change ""

to ----.

Col. 7, line 16:     change "23of" to -- 23% of --.

UNITED STATES PATENT AND TRADEMARK OFFICE
CERTIFICATE OF CORRECTION

PATENT NO. : 5,171,679

DATED : December 15, 1992

INVENTOR(S) : Erasmus Huber, et al.

It is certified that error appears in the above-identified patent and that said Letters Patent is hereby corrected as shown below:

Col. 11, claim 1 formula (11A):

and

Col. 14, line 17 (claim 11) formula (11A):

Col. 12, line 45:    delete "NH-NH" and insert -- NH-(-NH --.

Col. 12 line 58: (formula claim 7)    near far right hand side "d", change "CONH$_2$ to --CONH- --.

UNITED STATES PATENT AND TRADEMARK OFFICE
CERTIFICATE OF CORRECTION

PATENT NO. : 5,171,679

DATED : December 15, 1992

INVENTOR(S) : Erasmus Huber, et al.

It is certified that error appears in the above-identified patent and that said Letters Patent is hereby corrected as shown below:

Col. 12, last line:  change "CONH" to -- $CONH_2$ --.

Col. 12, line 49:  change "8" to -- 1 --.

Col. 13, line 40 (claim 11):  change "NH-NH" to -- NH-(-NH --.

Signed and Sealed this

Twenty-sixth Day of December, 1995

Attest:

BRUCE LEHMAN

Attesting Officer    Commissioner of Patents and Trademarks